US00PP32171P3

(12) United States Plant Patent
Post

(10) Patent No.: US PP32,171 P3
(45) Date of Patent: Sep. 8, 2020

(54) ***CHRYSANTHEMUM* PLANT NAMED 'DLFMGNM2'**

(50) Latin Name: ***Chrysanthemum* X *morifolium***
Varietal Denomination: DLFMGNM2

(71) Applicant: Arie Gerard Post, Delft (NL)

(72) Inventor: Arie Gerard Post, Delft (NL)

(73) Assignee: Deliflor Royalties B.V., Maasdijk (NL)

( * ) Notice: Subject to any disclaimer, the term of this patent is extended or adjusted under 35 U.S.C. 154(b) by 0 days.

(21) Appl. No.: 16/602,042

(22) Filed: Jul. 25, 2019

(65) Prior Publication Data

US 2020/0053933 P1 Feb. 13, 2020

Related U.S. Application Data

(60) Provisional application No. 62/764,554, filed on Aug. 7, 2018.

(51) Int. Cl.
*A01H 5/02* (2018.01)
*A01H 6/14* (2018.01)

(52) U.S. Cl.
USPC ..... Plt./289
CPC ..... *A01H 6/1424* (2018.05)

(58) Field of Classification Search
USPC ..... Plt./263.1, 284, 286, 287, 289
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Chrysanthemum* plant named 'DLFMGNM2', characterized by its upright plant habit; vigorous growth habit; dark green-colored leaves; uniform flowering habit; strong upright flowering stems typically grown as a disbud-type with one inflorescence per lateral branch; large incurved decorative-type inflorescences with bright yellow-colored ray florets; excellent postproduction longevity; and tolerance to low and high temperatures.

2 Drawing Sheets

Botanical designation: *Chrysanthemum* X *morifolium.*
Cultivar denomination: 'DLFMGNM2'.

CROSS-REFERENCED TO CLOSELY RELATED APPLICATIONS

Title: Varieties of *Chrysanthemum* Plants
Applicant: Arie Gerard Post
Provisional application Ser. No. 62/764,554
Filed: Aug. 7, 2018.

BACKGROUND OF THE INVENTION

The present invention relates to a new and distinct cultivar of *Chrysanthemum* plant, botanically known as *Chrysanthemum* X *morifolium,* commercially grown as a cut flower and hereinafter referred to by the name 'DLFMGNM2'.

The new *Chrysanthemum* plant is a product of a planned breeding program conducted by the Inventor in Maasdijk, The Netherlands. The objective of the breeding program is to create new cut *Chrysanthemum* plants with attractive inflorescences, strong flowering stems and excellent post-production longevity.

The new *Chrysanthemum* plant is a naturally-occurring whole plant mutation of *Chrysanthemum* x *morifolium* 'DLFMGNM1', not patented. The new *Chrysanthemum* plant was discovered and selected as a single flowering plant from within a population of plants of 'DLFMGNM1' in a controlled greenhouse environment in Maasdijk, The Netherlands on Apr. 25, 2016.

Asexual reproduction of the new *Chrysanthemum* plant by vegetative terminal cuttings since Apr. 25, 2016 has shown that the unique features of this new *Chrysanthemum* plant are stable and reproduced true to type in successive generations of asexual reproduction.

SUMMARY OF THE INVENTION

Plants of the new *Chrysanthemum* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'DLFMGNM2'. These characteristics in combination distinguish 'DLFMGNM2' as a new and distinct *Chrysanthemum* plant:

1. Upright plant habit; vigorous growth habit.
2. Dark green-colored leaves.
3. Uniform flowering habit.
4. Strong upright flowering stems typically grown as a disbud-type with one inflorescence per lateral branch.
5. Large incurved decorative-type inflorescences with bright yellow-colored ray florets.
6. Excellent postproduction longevity.
7. Relatively tolerant to low and high temperatures.

Plants of the new *Chrysanthemum* differ primarily from plants of the mutation parent, 'DLFMGNM1', in ray floret color as plants of the new *Chrysanthemum* have bright yellow-colored ray florets whereas plants of 'DLFMGNM1' are white in color. In addition, ray florets of plants of the new *Chrysanthemum* are more twisting than ray florets of 'DLFMGNM1'.

Plants of the new *Chrysanthemum* can be compared to plants of *Chrysanthemum* X *morifolium* 'Zembla Yellow', disclosed in U.S. Plant Pat. No. 14,733. In side-by-side comparisons plants of the new *Chrysanthemum* differ primarily from plants of 'Zembla Yellow' in the following characteristics:

1. Plants of the new *Chrysanthemum* have larger inflorescences than plants of 'Zembla Yellow'.
2. Ray florets of plants of the new *Chrysanthemum* are brighter yellow in color than ray florets of plants of 'Zembla Yellow'.

Plants of the new *Chrysanthemum* can also be compared to plants of *Chrysanthemum* X *morifolium* 'DLFGAGA1', not patented. In side-by-side comparisons plants of the new *Chrysanthemum* differ primarily from plants of 'DLFGAGA1' in ray floret color as ray florets of plants of the new *Chrysanthemum* are more bright yellow in color whereas ray florets of plants of 'DLFGAGA1' are white in color.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'DLFMGNM2' grown as a disbud-type.

The photograph on the second sheet comprises close-up views of the lower (top of the photographic sheet) and upper surfaces (bottom of the photographic sheet) of typical inflorescences and leaves of 'DLFMGNM2'.

DETAILED BOTANICAL DESCRIPTION

The aforementioned photographs and following observations and measurements describe plants grown during the spring in ground beds in a glass-covered greenhouse in Maasdijk, The Netherlands and under cultural practices typical of commercial cut *Chrysanthemum* production. Plants were initially given long day/short night treatments followed by short day/long night treatments to induce flower initiation and development. During the production of the plants, day temperatures ranged from 18° C. to 22° C., night temperatures ranged from 20° C. to 25° C. and light levels averaged 8 klux. Plants were grown as single-stem disbud-type plants and were ten weeks old when the photographs and the description were taken. In the following description, color references are made to The Royal Horticultural Society Colour Chart, 2015 Edition, except where general terms of ordinary dictionary significance are used.

Botanical classification: *Chrysanthemum* X *morifolium* 'DLFMGNM2'.

Parentage: Naturally-occurring whole plant mutation of *Chrysanthemum* x *morifolium* 'DLFMGNM1', not patented.

Propagation:

*Type.*—Terminal vegetative cuttings.

*Time to initiate roots, summer.*—About six days at temperatures about 24° C.

*Time to initiate roots, winter.*—About eight days at temperatures about 22° C.

*Time to produce a rooted young plant, summer.*—About twelve days at temperatures about 24° C.

*Time to produce a rooted young plant, winter.*—About two weeks at temperatures about 22° C.

*Root description.*—Fine, fibrous; typically creamy white in color, actual color of the roots is dependent on substrate composition, water quality, fertilizers, substrate temperature and physiological age of roots.

*Rooting habit.*—Freely branching, medium density.

Plant description:

*Plant and growth habit.*—Herbaceous incurved decorative-type cut flower that is typically grown as a single stem disbud-type; upright plant habit; vigorous growth habit and moderate to rapid growth rate.

*Plant height, soil level to top of foliar plane.*—About 81.8 cm.

*Plant height, soil level to top of inflorescence plane.*—About 87.3 cm.

*Plant diameter (foliar).*—About 22.7 cm.

*Plant diameter (floral).*—About 14.4 cm.

*Flowering stem length.*—About 81.8 cm.

*Flowering stem diameter.*—About 7 mm.

*Flowering stem internode length.*—About 2.7 cm.

*Flowering stem strength.*—Strong.

*Flowering stem aspect.*—Erect.

*Flowering stem texture and luster.*—Moderately pubescent; slightly glossy.

*Flowering stem color, developing.*—Close to 143C, at the internodes, close to 147C.

*Flowering stem color, developed.*—Close to 147C and 147D.

*Leaf description.*—Arrangement: Alternate; simple. Length: About 14.4 cm. Width: About 7.5 cm. Shape: Oblong to elliptic. Apex: Short apiculate. Base: Narrowly attenuate. Margin: Palmately lobed, coarsely serrate to dentate; sinuses convergent and shallow to medium in depth. Texture and luster, upper surface: Moderately to densely pubescent, not rugose; moderately velvety; slightly glossy. Texture and luster, upper surface: Moderately to densely pubescent, prominent venation; moderately velvety; slightly glossy. Venation pattern: Pinnate, reticulate. Color: Developing leaves, upper surface: Close to 143B. Developing leaves, lower surface: Close to 146B. Fully developed leaves, upper surface: Close to NN137A; venation, close to 146B. Fully developed leaves, lower surface: Close to 147B; venation, close to 146D. Petioles: Length: About 2 cm. Diameter: About 3 mm by 5 mm. Strength: Moderately strong. Texture and luster, upper and lower surfaces: Moderately to densely pubescent; moderately glossy. Color, upper surface: Close to 146D; edges, close to 143A. Color, lower surface: Close to 146D; edges, close to 147B. Stipules: Quantity and appearance: Two leafy stipules, opposite, at the petiole attachment to the stem. Length: About 8 mm. Width: About 6 mm. Shape: Obovate. Apex: Short apiculate. Base: Cuneate. Texture and luster, upper surface: Moderately to densely pubescent, not rugose; moderately velvety; slightly glossy. Texture and luster, upper surface: Moderately to densely pubescent, prominent venation; moderately velvety; slightly glossy. Color: Upper surface: Close to NN137A; venation, close to 146B. Lower surface: Close to 147B; venation, close to 146D.

Inflorescence description:

*Appearance.*—Incurved inflorescence form with oblanceolate-shaped ray florets; inflorescences borne perpendicular to peduncles and face mostly upright; ray and disc florets develop acropetally on a capitulum.

*Fragrance.*—Faintly fragrant; sweet.

*Flowering response.*—Under natural conditions, plant flower in the autumn/winter in the Northern Hemisphere; at other times of the year, inflorescence initiation and development can be induced under short day/long night conditions (at least 13.5 hours of darkness); plants exposed to two weeks of long day/short night conditions after planting followed by photoinductive short day/long night conditions flower about 70 days later when grown as a spray-type; uniform flowering habit.

*Postproduction longevity.*—Good postproduction longevity; in an interior environment, inflorescences and foliage will maintain good color and substance for about two weeks; inflorescences persistent.

*Quantity of inflorescences.*—Typically grown as a disbud type therefore, only the terminal inflorescence develops.

*Inflorescence size.*—Diameter: About 14.4 cm. Depth (height): About 9.9 cm. Disc diameter: About 8 mm, inconspicuous.

*Receptacles.*—Height: About 6 mm. Diameter: About 1.5 cm. Shape: Flattened globular. Color: Close to 191A.

*Inflorescence buds.*—Height: About 7 mm. Diameter: About 1.4 cm. Shape: Flattened globular. Texture and luster: Smooth and glabrous; matte. Color: Close to 137B and 138A.

*Ray florets.*—Quantity and arrangement: About 530 arranged in about 15 whorls. Length: About 2.8 cm to 7.8 cm. Width: About 0.5 cm to 1.9 cm. Shape: Oblanceolate; strongly concave. Apex: Bluntly acute. Base: Attenuate. Margin: Entire; not undulate. Aspect: Initially upright to eventually about 60° from vertical. Texture and luster, upper surface: Smooth, glabrous; moderately velvety; not rugose; matte. Texture and luster, lower surface: Smooth, glabrous; slightly velvety; not rugose; slightly glossy. Color: When opening, upper surface: Close to 1A; towards the base, close to 3D. When opening, lower surface: Close to 2D; towards the apex, close to 1B. Fully opened, upper surface: Close to 2D; venation, close to 2D; color does not change with development. Fully opened, lower surface: Close to 4D; venation, close to 4D; color does not change with development.

*Disc florets.*—Quantity and arrangement: About 40 spirally arranged in about four whorls at the center of the receptacle. Length: About 7.5 mm. Diameter: About 1.25 mm. Shape: Lower 80% fused into a tube; upper 20% free. Apex: Bluntly acute. Margin: Entire. Texture and luster, inner and outer surfaces: Smooth, glabrous; not rugose; glossy. Color, when opening, inner and outer surfaces: Apex: Close to N144C. Mid-section: Close to 145D. Base: Close to 150D. Color, fully opened, inner and outer surfaces: Apex: Close to N144C. Mid-section: Close to 145D. Base: Close to 150D.

*Involucral bracts.*—Quantity and arrangement: About 50 arranged in three whorls. Length: About 1.5 cm. Width: About 4 mm. Shape: Narrowly ovate to narrowly deltoid. Apex: Obtuse. Base: Cuneate. Margin: Entire. Texture and luster, upper surface: Smooth, glabrous; glossy. Texture and luster, lower surface: Sparsely pubescent; matte. Color, upper surface: Close to 146B; margins, translucent, and close to 157D; apices, close to N199A. Color, lower surface: Close to 137A; margins, translucent, close to 157D; apices, close to N199A.

*Peduncles.*—Length: About 3.5 cm. Diameter: About 7 mm. Strength: Strong. Aspect: Mostly upright. Texture and luster: Moderately pubescent; matte. Color: Close to between 143B and 144A.

*Reproductive organs.*—Androecium: Present on disc florets only. Quantity: About five per floret. Filament length: About 2 mm. Filament color: Close to 150D. Anther size: About 0.5 mm by 1.5 mm. Anther shape: Narrowly oblong. Anther color: Close to 161A. Pollen amount: None observed. Gynoecium: Present on both ray and disc florets. Quantity: One per floret. Pistil length: About 8 mm. Style length: About 7 mm. Style color: Close to 150B. Stigma diameter: About 1 mm. Stigma shape: Cleft, decurrent. Stigma color: Close to 154B to 154C. Ovary color: Close to 145D.

*Seeds and fruits.*—To date, seed and fruit production have not been observed on plants of the new *Chrysanthemum.*

Pathogen & pest resistance: To date, resistance to pathogens and pests common to *Chrysanthemum* plants has not been observed on plants of the new *Chrysanthemum* grown under commercial conditions.

Temperature tolerance: Plants of the new *Chrysanthemum* have been observed to tolerate temperatures ranging from about −12° C. to 35° C. and to be suitable for USDA Hardiness Zones 8 to 10.

It is claimed:

1. A new and distinct *Chrysanthemum* plant named 'DLFMGNM2' as illustrated and described.

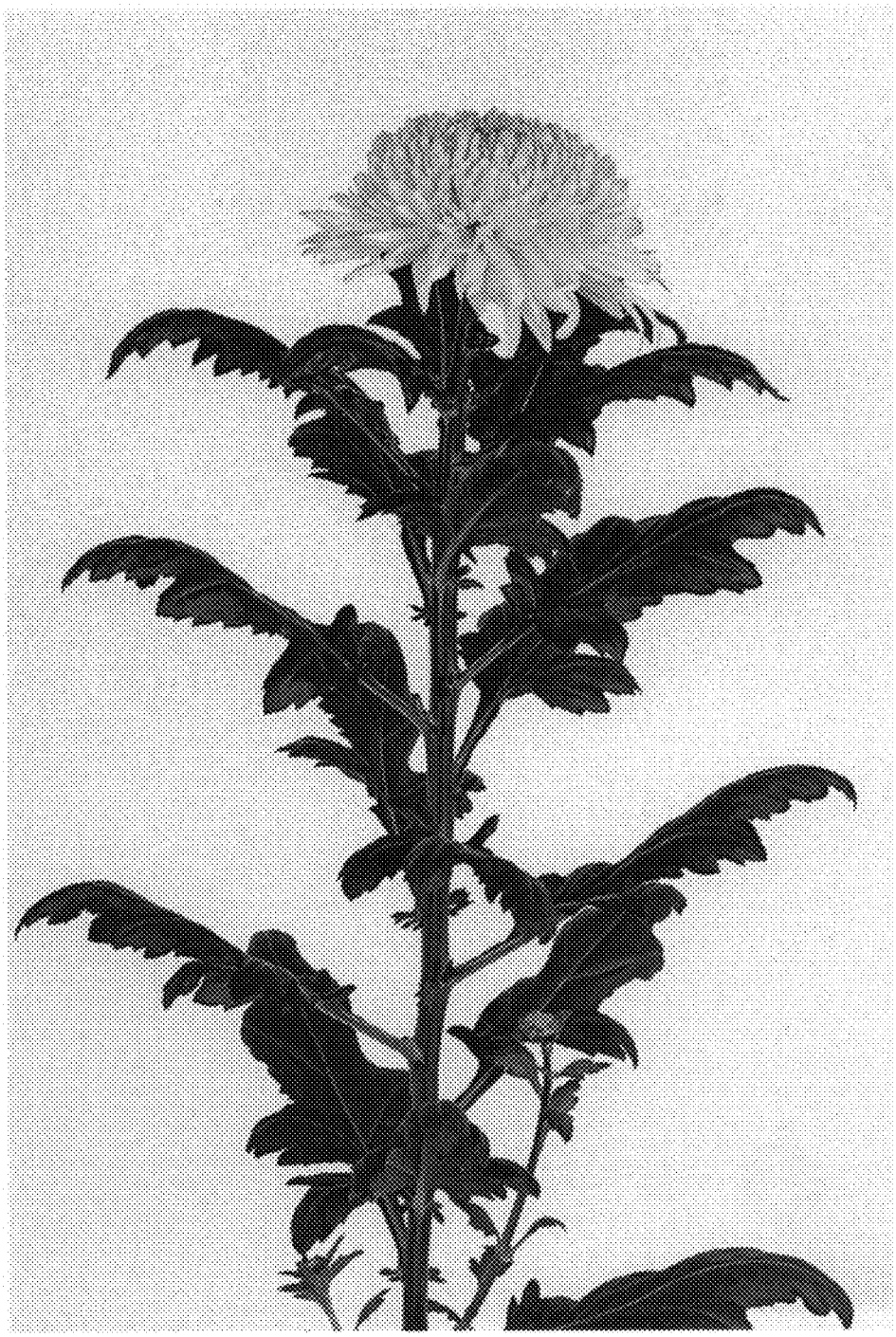

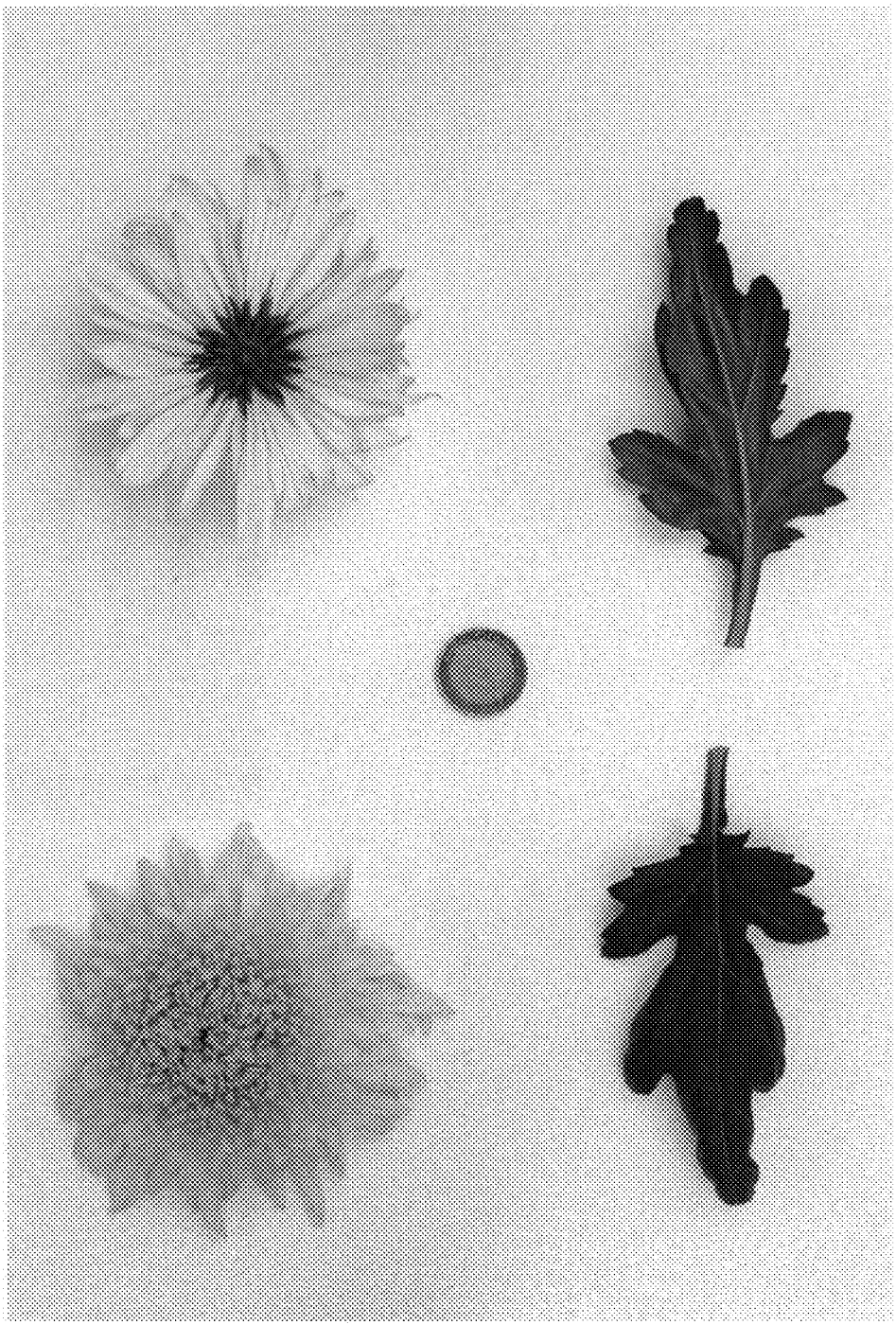

* * * * *